United States Patent [19]

Tack

[11] Patent Number: 5,620,159
[45] Date of Patent: Apr. 15, 1997

[54] HANGER ASSEMBLY FOR LIQUID IRRIGATOR AND SLEEVE

[76] Inventor: Carl E. Tack, 407 Ashland Ave., River Forest, Ill. 60305

[21] Appl. No.: 543,023

[22] Filed: Oct. 13, 1995

[51] Int. Cl.⁶ .................................................. A47B 96/06
[52] U.S. Cl. ......................................... 248/214; 248/340
[58] Field of Search .................................. 248/214, 215, 248/317, 327, 340, 339, 227.1, 304, 303

[56] References Cited

U.S. PATENT DOCUMENTS

| | | | |
|---|---|---|---|
| 2,606,734 | 8/1952 | Magnuson | 248/215 |
| 3,672,370 | 6/1972 | Marsan | 604/333 X |
| 3,830,235 | 8/1974 | Marsan | 604/333 X |
| 4,047,687 | 9/1977 | Turner | 248/333 X |
| 4,738,369 | 4/1988 | Desjardins | 248/333 X |
| 5,427,343 | 6/1995 | Ferris | 248/215 |

*Primary Examiner*—Ramon O. Ramirez
*Attorney, Agent, or Firm*—Juettner Pyle Lloyd & Piontek

[57] ABSTRACT

A hanger assembly is provided for adjustably supporting an irrigator bag and allowing hanging and drying of an irrigator sleeve. The assembly includes a rod having two hooks at the top, a downwardly facing hook for hanging the rod and an upwardly facing hook for hanging the sleeve. A hanger arm is slidably mounted on the rod. The rod has a number of openings which may be engaged by a pin in the hanger arm to allow adjustment of the height of the arm.

2 Claims, 2 Drawing Sheets

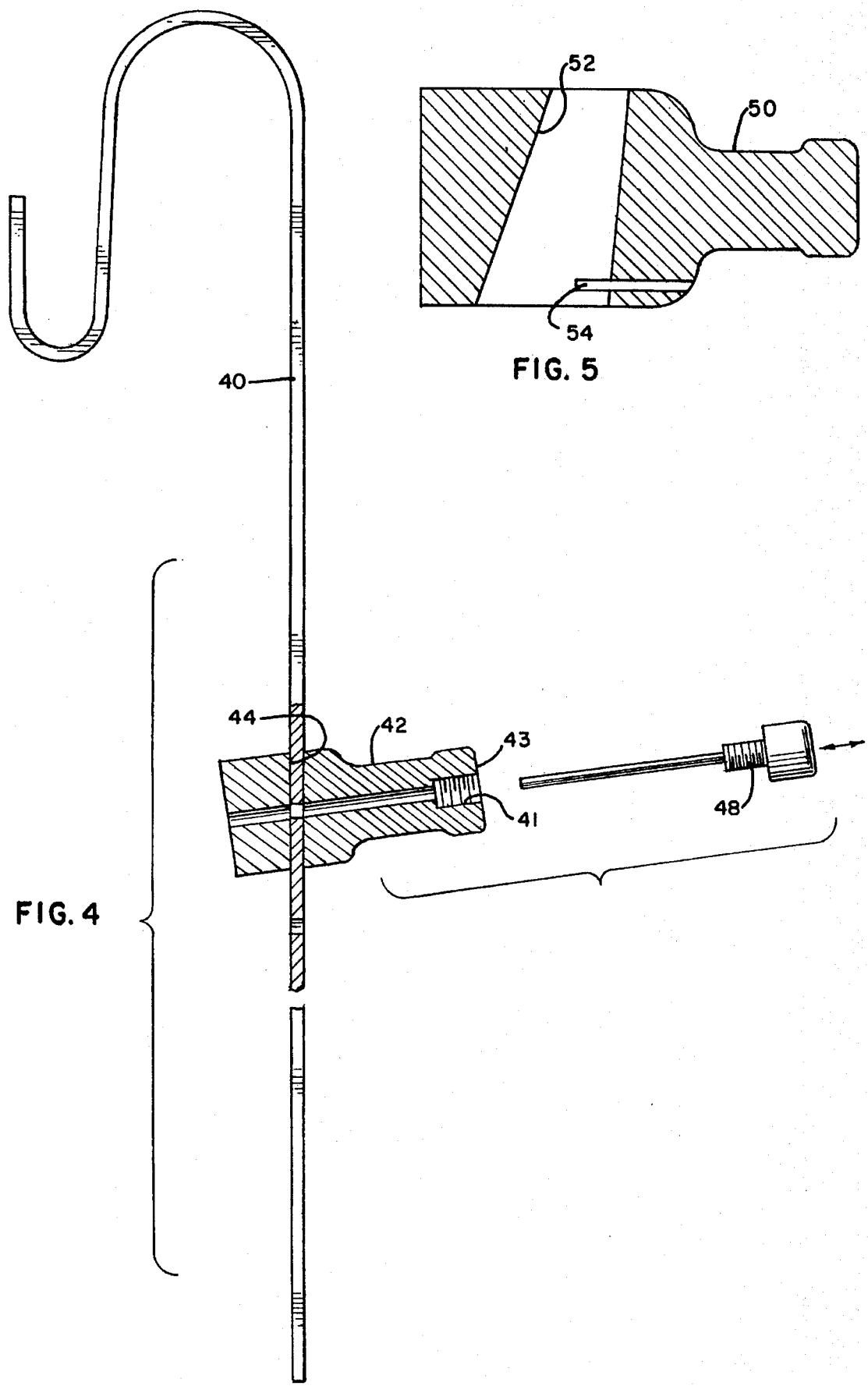

HANGER ASSEMBLY FOR LIQUID IRRIGATOR AND SLEEVE

BACKGROUND OF THE INVENTION

The present invention relates to a hanger for the support of a liquid container connected to a tube and used to irrigate internal parts of the body, such as a douche or enema bag, or irrigation of a colostomy. It is well known to support liquid containing bags of this nature from short s-shaped hooks, which can be hooked through an aperture in the bag and over a stationary support, such as a towel bar, shower curtain rod, or top of shower door frame. The height of the supported bag relative to the user is very important, and if the distance above the user is too great, the hydrostatic pressure will be excessive and the rate of liquid flow through the tube will be excessive.

Irrigation of a colostomy also requires the use of a flexible plastic sleeve. The hooks in present use do not have any provision for hanging the sleeve for drainage after it has been rinsed.

A third problem is that conventional S hooks in current use have a small cross section and tend to tear the bag.

SUMMARY OF THE INVENTION

In accordance with the present invention, a hanger for a liquid irrigating bag is provided in the form of a cane-shaped member, with a top downwardly facing hook portion and a leg extending downwardly therefrom. A second upwardly facing irrigator sleeve hanging hook is preferably provided from the free end of the downwardly facing hook. Thus, if the hanger is hooked over a shower curtain rod, for example, the sleeve draped over the second hook will drain into the shower or bathtub.

The downwardly extending leg is provided with an arm slidably and adjustably mounted on the leg, for supporting the liquid bag. The arm may have a relatively large knob or terminus to better retain the bag and prevent it from slipping off and may be inclined slightly upwardly.

Means are provided for fixing the hanger arm to the leg in the desired adjusted position. For example, a line of holes may be provided along the length of the leg, and the arm may have a pin associated therewith engageable in one of the holes.

For convenience while traveling, the hanger may be made of parts which can be disassembled and reassembled.

BRIEF DESCRIPTION OF THE DRAWINGS

FIG. 4 is a vertical sectional view of another embodiment leg having an internal pin of the hanger assembly of the present invention.

FIG. 5 is a sectional view through an alternative embodiment of a hanger leg.

DESCRIPTION OF THE PREFERRED EMBODIMENTS

Figure 2:
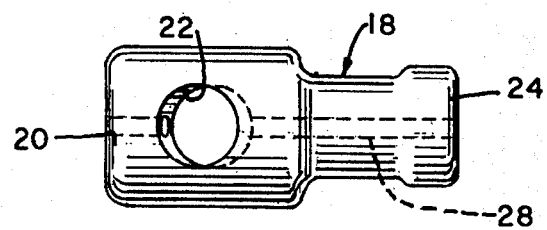
FIG. 2 is a top view of the adjustable hook or hanger leg shown in the assembly of FIG. 1.
Figure 1:
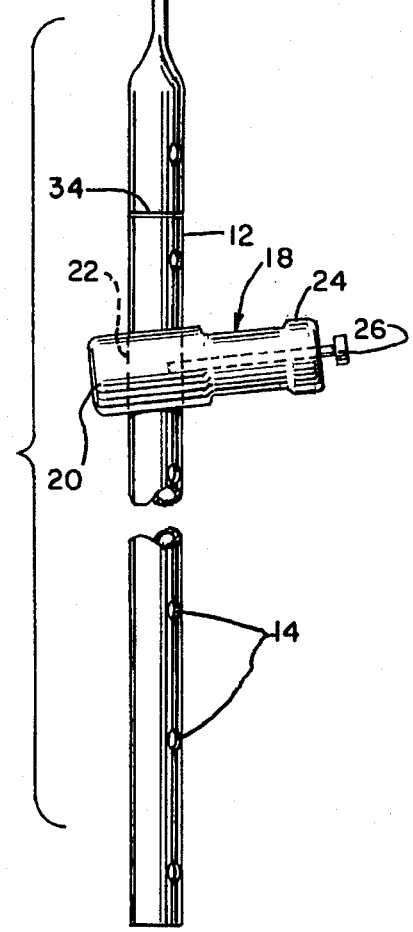
FIG. 1 is a side view of the hanger assembly of the present invention.

As shown in FIGS. 1 and 2, a first embodiment of the hanger assembly comprises an upper, downwardly facing hook portion 10 formed of flat stock, with the hook portion extending to a lower elongated tube or rod portion 12 having a plurality of apertures 14. The spaced apertures extend along a line parallel to the longitudinal axis of the rod. The free end of the upper hook portion 10 is also preferably bent upwardly to provide a second, upwardly facing hook 16. When the assembly is, for example, hung over a shower rod, the secondary hook 16 will extend over the tub or shower stall, and an irrigator sleeve may be draped over the secondary hook.

A hanger arm 18 having a base 20 is slidably mounted on the tube portion by means of a vertical aperture 22 through the base. Preferably, aperture 22 is formed at an acute angle with respect to vertical, as shown, such that the arm 18 is tilted slightly upwardly when the arm is engaged with the tubular portion, to prevent an irrigator bag from falling off the arm. The arm 18 thus extends outwardly and slightly upwardly and terminates in a free end 24, which may be slightly enlarged for additional security.

Means are provided for adjustably securing the hanger arm 18 at the desired location on the tubular portion 12. This may take the form of an axially movable pin 26 inserted through an opening 28 through the body of the arm and into one of the apertures 14 in the tubular portion 23. Thus, the arm can be adjusted to any desired height by simply withdrawing the pin 26 sufficiently to enable the arm to be moved to a different position on the tube, and then reengaging the pin.

Figure 3:
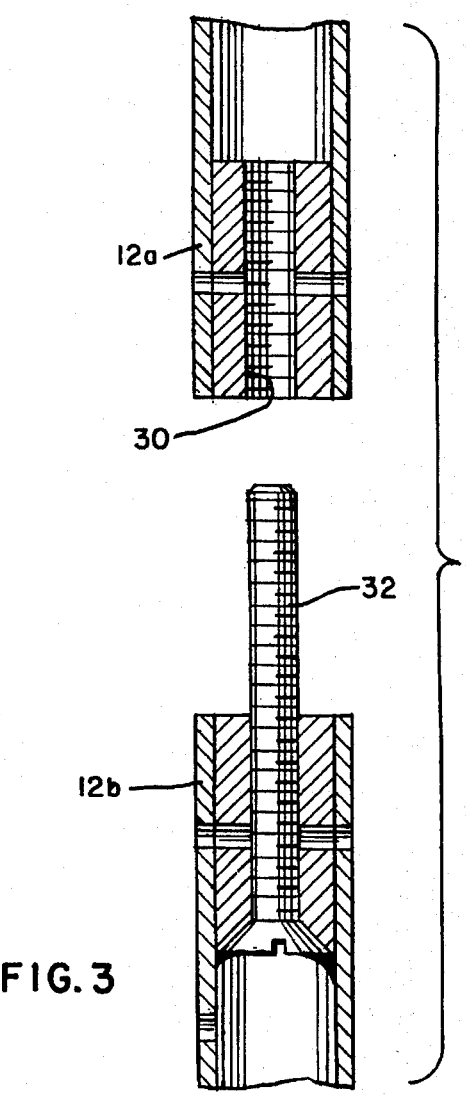
FIG. 3 is a vertical sectional view of a portion of the assembly shown in FIG. 1.

FIG. 3 illustrates the possibility of making the tubular portion 12 into sections 12a and 12b in which the sections are provided with internal engageable female 30 and projecting male 32 thread members, which are screwed together to provide a joint 34 (FIG. 1). This feature enables the hanger rod portion to be disassembled into two or more pieces, which is convenient for storage and travel.

FIG. 4 illustrates another embodiment in which the entire body of the hanger is made from flat stock 40, and the arm 42 has a slot-like aperture 4d therein whereby the arm is slidably received on the hanger. In the embodiment shown, the pin 46 has a male threaded portion 48 which can be threaded into a female threaded portion 41 in the end 43 of the arm.

FIG. 5 shows a modified arm 50 having a round, inclined opening 52 for mounting the arm on the tube 12 shown in FIG. 1. In this case, the opening 52 is flared to a larger diameter from top to bottom to enable the arm to be tilted upwardly on the tube. A stationary pin 54 extends into a lower portion of the opening 52 in such a fashion that the pin is opposed to the series of apertures 14 and is engageable therewith. This version eliminates the need to manually retract a pin when a height adjustment is made.

It will be noted in all embodiments, for example in FIG. 1, that the hooked portion 10 of the rod 12 and the hanger arm 18 are preferably arranged in a substantially common plane, with the hook 10 and arm 18 extending laterally from the rod 12 in opposite directions in order to provide adequate clearance from the support structure on which the hook 10 is supported. Thus, the line of apertures 14 falls substantially within the same plane.

What is claimed is:

1. Hanger assembly for liquid irrigator and sleeve, said assembly comprising a hanger rod comprising an upper downwardly facing hook portion, an elongated downwardly extending rod portion having a longitudinal axis extending from said upwardly facing hook portion, an upwardly facing hook extending laterally from said downwardly facing hook, a hanger arm slidably mounted on said rod portion, a plurality of openings in said rod portion along said longitudinal axis, and a pin associated with said hanger arm for engaging one of said openings, whereby said hanger arm may be adjustably positioned on said rod portion.

2. The hanger assembly of claim 1 additionally comprising means for securing said pin to said hanger arm.

* * * * *